(12) United States Patent
Moustafa

(10) Patent No.: US 9,486,217 B2
(45) Date of Patent: Nov. 8, 2016

(54) MAGNETIC WOUND CLOSURE DEVICE AND METHOD OF USE

(71) Applicant: Moustafa Moustafa, Beverly Hills, CA (US)

(72) Inventor: Moustafa Moustafa, Beverly Hills, CA (US)

( * ) Notice: Subject to any disclaimer, the term of this patent is extended or adjusted under 35 U.S.C. 154(b) by 519 days.

(21) Appl. No.: 14/033,716

(22) Filed: Sep. 23, 2013

(65) Prior Publication Data

US 2015/0088195 A1 Mar. 26, 2015

(51) Int. Cl.
*A61L 15/26* (2006.01)
*A61L 15/42* (2006.01)
*A61B 17/08* (2006.01)
*A61B 17/00* (2006.01)

(52) U.S. Cl.
CPC .............. *A61B 17/085* (2013.01); *A61L 15/26* (2013.01); *A61L 15/42* (2013.01); *A61B 2017/00876* (2013.01)

(58) Field of Classification Search
CPC ................ A61B 17/085; A61B 17/08; A61B 17/12013; A61B 17/1285; A61B 17/122; A61B 2017/00876; A61B 17/083
See application file for complete search history.

(56) References Cited

U.S. PATENT DOCUMENTS

| 4,825,866 | A | | 5/1989 | Pierce | |
|---|---|---|---|---|---|
| 5,423,736 | A | * | 6/1995 | Cartmell | A61B 17/085 602/42 |
| 5,478,308 | A | * | 12/1995 | Cartmell | A61B 17/085 602/42 |
| 7,556,632 | B2 | | 7/2009 | Zadno | |
| 8,267,959 | B2 | | 9/2012 | Fällman | |
| 2005/0228442 | A1 | | 10/2005 | Wheatley | |
| 2009/0036922 | A1 | * | 2/2009 | Riskin | A61B 17/083 606/215 |
| 2010/0100022 | A1 | * | 4/2010 | Greener | A61B 17/083 602/44 |
| 2010/0268270 | A1 | | 10/2010 | Viola | |
| 2012/0095502 | A1 | | 4/2012 | Bargon | |

* cited by examiner

*Primary Examiner* — Tuan V Nguyen
*Assistant Examiner* — Chima Igboko
(74) *Attorney, Agent, or Firm* — Trojan Law Offices

(57) ABSTRACT

A wound closure device using magnets to draw skin together without using stitches. When two skin adhering magnets are placed on opposite sides of a wound in a polar opposite configuration, the magnets attract each other, thus drawing the skin underneath the magnets together. Each device has a magnet, an insulation layer that separates the magnet from an absorbent layer that absorbs wound secretions, a polymer layer having a plurality of holes that allow drainage of potential build-up secretions away from the absorbent layer, and an adhesive layer on the bottom that allows the device to adhere to the patient's skin. The device may be enclosed within a polymer casing that use flexible magnets, or a plurality of segmented magnets to help align the device along a non-linear (curved) wound.

11 Claims, 3 Drawing Sheets

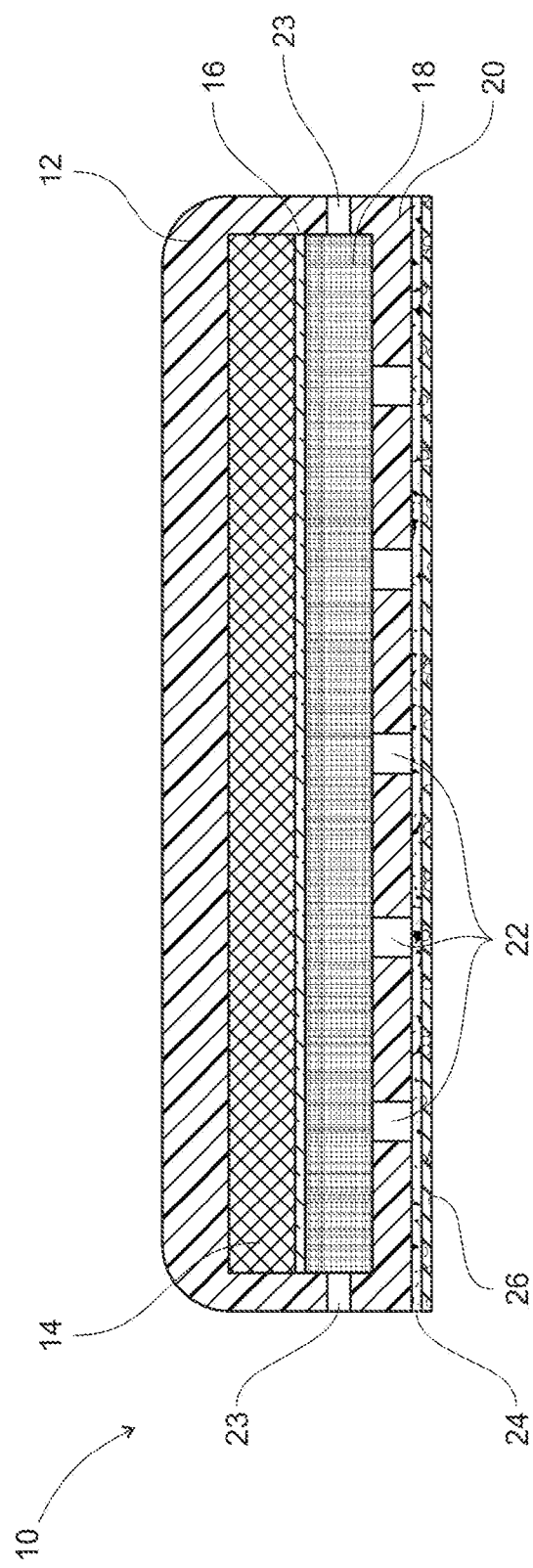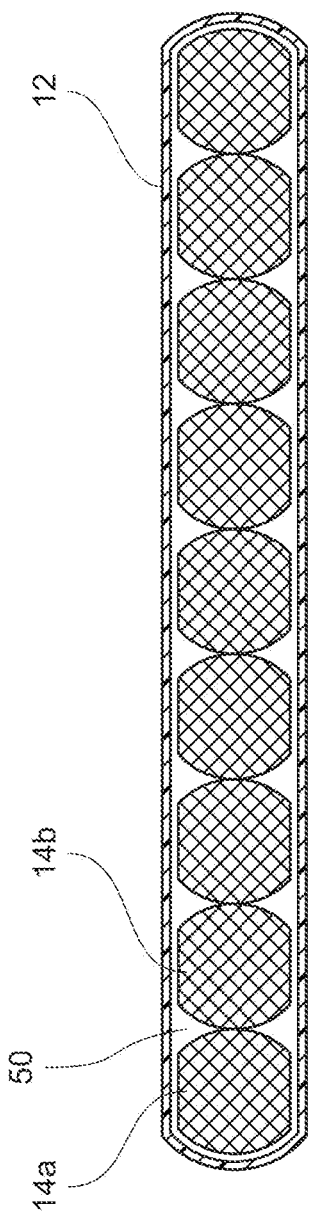

MAGNETIC WOUND CLOSURE DEVICE AND METHOD OF USE

FIELD OF THE INVENTION

The present invention relates generally to a device useful for wound healing, and more particularly to a magnetic device that draws wound edges in proximity to each other.

BACKGROUND OF THE INVENTION

Wounds usually occur when there is trauma to the skin and underlying tissue. Types of trauma include lacerations, abrasions, incisions, punctures, and penetrations. After trauma, the wound begins to heal in a complex series of biochemical processes occurring is several wound-healing phases. The phases of healing are often categorized into a hemostasis phase, an inflammatory phase, a proliferative phase and a remodeling phase. In hemostasis, active bleeding is controlled by clotting. In the inflammatory phase, pathogens are removed by the body away from the wounded area, and biological factors are released (which later cause the division of cells involved in the proliferative phase). In the proliferative phase, new blood vessels are formed and wound contraction occurs. Also in the proliferative phase, epithelial cells cover the wound, providing an area of growth for new tissue. During contraction, the wound is made smaller by myofibroblasts attaching to the wound edges, and finally, during the remodeling phase, collagen fibers are realigned along tension lines formed during the earlier phases of healing.

Not only is the process of wound healing complex, but it is also fragile, since many factors can lead to a disruption of proper wound healing, including re-injury of the tissue, bacterial infection, and physical stress on the damaged tissue. A variety of devices and methods have been used to aid in the wound healing process. These devices and methods are generally divided into one of three types: primary intention, secondary intention, and tertiary intention. The primary intention devices and methods bring the edges of the wounds together, so that the edges are reapproximated. Reapproximation helps to minimize scarring, and increases the speed at which wound contraction and healing occur. Examples of primary intention devices and methods include the use sutures, staples, tape, glue, and hooks. Primary intention techniques to heal wounds are the most common techniques used by practitioners. While not as commonly used, secondary intention devices and methods include first allowing the wound granulate without closing the wound, and thereafter packing and draining the wound several times to remove debris. Still less common are tertiary intension devices and methods, which delay the closure of the wound even longer, so that the practitioner can close the wound at a later time. Tissue grafting is an example of a tertiary method for wound healing.

Wound edge reapproximation is key to wound healing. If the edges of the wound are not immediately reapproximated soon after injury, healing may be delayed. This delay in healing may leads to scarring and infection. While in some circumstances a delay is advantageous, practitioners generally want to close an open wound as soon as possible. Therefore, quick and easy to use devices and methods are needed to reapproximate the wound edges.

The traditional method to reapproximate wound edges is by sutures, where a practitioner stitches a threading material to connect opposing sides of a wound. Sutures and suturing techniques are well known in the prior art, such as described in U.S. Pat. No. 8,267,959. Other devices and methods to reapproximate wound edges include hooking devices, such as the hook closure device in in U.S. patent application Ser. No. 13/266,825, where a band placed over a wound has a multiplicity of hook elements that engage a mesh on the opposing side of a wound.

The use of adhesive strips is another method to aid in wound closure. In U.S. Pat. No. 4,825,866, adhesive strips are placed on opposite sides of a wound and drawn together to reapproximate the wound edges. Stapling and clipping the edges of wound are other techniques to reapproximate wound edges, as described in U.S. Pat. No. 7,556,632.

The use of magnets to reapproximate wound edges has also previously been described. U.S. patent application Ser. Nos. 10/512,964 and 12/721,651 are two applications that have described tissue joining devices comprising interconnecting components where the magnetic components are attracted to each other and draw tissue together using magnetism.

Other compositions and methods to reapproximate wound edges include the use of medical adhesives, such as cyanoacrylate glues that provide for very tight, high-strength closure of wounds without the need for the physical closure accomplished with sutures. However, cyanoacrylate based glues have been associated with the formation of toxic byproducts, and even non-toxic versions are generally only useful for smaller, shallow lacerations in low-tension areas. These adhesives can be very unforgiving if the practitioner needs to remove the glue. Another disadvantage of using glues for wound closure is that leakage of glues can cause serious ramifications, especially if the adhesives are toxic and the wounds are near sensitive anatomical structures, such as the eye. Still another disadvantage is that adhesives can trap pathogens and other particles within the wound.

Each type of wound closure device and technique has advantages and disadvantages. Sutures pose the risk of needle stick injury to the patient, as well as to health care professions. The process of suturing also can take a substantial amount of time depending on the size of the wound. Using staples for wound closure is more rapid than suturing, however, unlike sutures, which may be absorbed by the body, staples usually have to be removed by a special tool. Sutures and staples also require applying local anesthesia, which could be painful and toxic to the patient. Furthermore, if the practitioner needs to enter the wound area, the sutures or staples need to be cut or removed, and both sutures and staples can lead to scarring.

Some of the more complex wound closure devices that reduce some of these disadvantages have many individual parts, are difficult to apply, or are expensive. Accordingly, it would be advantageous to make available a novel wound closure device that reduces these stated disadvantages.

SUMMARY OF THE INVENTION

The present invention relates to a wound closure device and methods of reapproximating wound edges, which lead to improved wound healing. It is an object of the present invention to provide a magnetic wound closure device, such that when two of the magnetic wound closure devices are attached to skin on opposites sides of a wound, the magnets attract each other, thereby pulling together the edges of the wound. There are several advantages to the described invention, including: 1) placement of the device on a patient is faster than using staples or sutures, 2) no need to wait for an anesthetic, less trauma, 3) no painful injections are needed, 4) inspection of the wound is simple because the device is easily removable, and 5) the device can be easily manufactured in a variety of sizes and shapes that accommodate various wound sizes.

The magnetic wound closure device is used as a pair of magnetic wound closure devices aligned in opposite polarity with respect to each other so that the magnetic edges of each device attracts the polar opposite edge of another device. In one embodiment, each of the magnetic wound closure devices has a magnet, an insulation layer adjacent to the magnet, an absorbent layer adjacent to the insulation layer, a polymer layer that has a plurality of holes capable of draining wound secretions to and from the absorbent layer, and an adhesive layer adjacent to the bottom surface of the polymer layer. The adhesive layer allows the magnetic wound closure device to adhere to the surface of the skin of a patient. When placed on the patient, the interior edges of each magnet are oriented in opposite polarity to each other, and on opposite sides of a wound (with the wound situated below and between two magnetic closure devices). Since the two magnetic wound closure devices are attached to the skin of the patient via an adhesive layer, when the two magnetic wound closure devices draw toward each other due to the magnetic forces between them, the skin edges surrounding the wound are drawn toward each other, thus making the wound opening smaller, thereby allowing the wound to heal more quickly.

In another embodiment, the magnetic wound closure device is enclosed within a polymer housing, which houses the magnet, insulation layer, and absorbent layer, and is contiguous with the polymer layer adjacent to the absorbent layer.

In yet another embodiment, the polymer layer and the polymer housing is a silicone polymer layer and a silicone polymer housing, respectively.

In yet another embodiment, the magnet is made from a plurality of segmented magnets capable of vertical and horizontal flexing. The plurality of segmented magnets allows the practitioner to curve and shape the device to the shape of the wound edges.

In yet another embodiment, the magnetic wound closure device has a removable adhesive cover that protects the adhesive layer. By covering the adhesive layer with the removable adhesive cover, the adhesive layer is protected until needed, and conserves the adhesive properties of the adhesive layer until the practitioner removes (such as by peeling off) the adhesive cover from the adhesive layer.

In still another embodiment of the invention, the wound closure device has a directional indicator marker for determining the correct directional alignment of the wound closure device with respect to the wound opening. In one embodiment of the directional indicators, the directional indicators are arrows pointing toward the edge of the magnetic device closest to the wound, such that when one magnetic device is placed on one edge of a wound with directional indicators pointing toward the wound, and a second magnetic device is placed on the opposite edge of the wound with directional indicators pointing toward the opposite wound edge, the pair of magnetic wound closure devices are oriented such that they attract, instead of repel each other. The directional indicators may point to the north pole magnetic end, the south pole magnetic end, and/or be color coded to help the practitioner determine the proper orientation of two magnetic wound closure devices with respect to each other and the wound.

It is another object of the invention to provide a method of reapproximating wound edges. The steps involve: adhering a first magnetic wound closure device on a patient substantially near a first edge of a wound, orienting a second wound closure device on a patient such that the inner edge of the second wound closure device is aligned in opposite polarity with the inner edge of the first wound closure device along a second (opposite) side of the same wound, and adhering the second wound closure device on the patient substantially near the second side of the wound. The inner edge of the first wound closure device and the inner edge of the second wound closure device attract each other due to aligning the magnetic wound closure devices in opposite polarity across a patient's wound.

In another embodiment of the method, adhering the magnetic wound closure devices on the patient is characterized as rolling the magnetic wound closure devices on the patient.

In another embodiment of the method, the user removes the adhesive cover from the wound closure device before the wound closure devices are placed on the patient.

BRIEF DESCRIPTION OF THE DRAWINGS

These and other features and advantages of the present invention will become appreciated, as the same becomes better understood with reference to the specification, claims and drawings herein:

FIG. 2 is a cross sectional view of FIG. 1.

FIG. 3 is a top cross sectional view of a segmented magnet that can be used as the magnetic layer in the magnetic wound closure device.

DETAILED DESCRIPTION OF THE INVENTION

Figure 1:
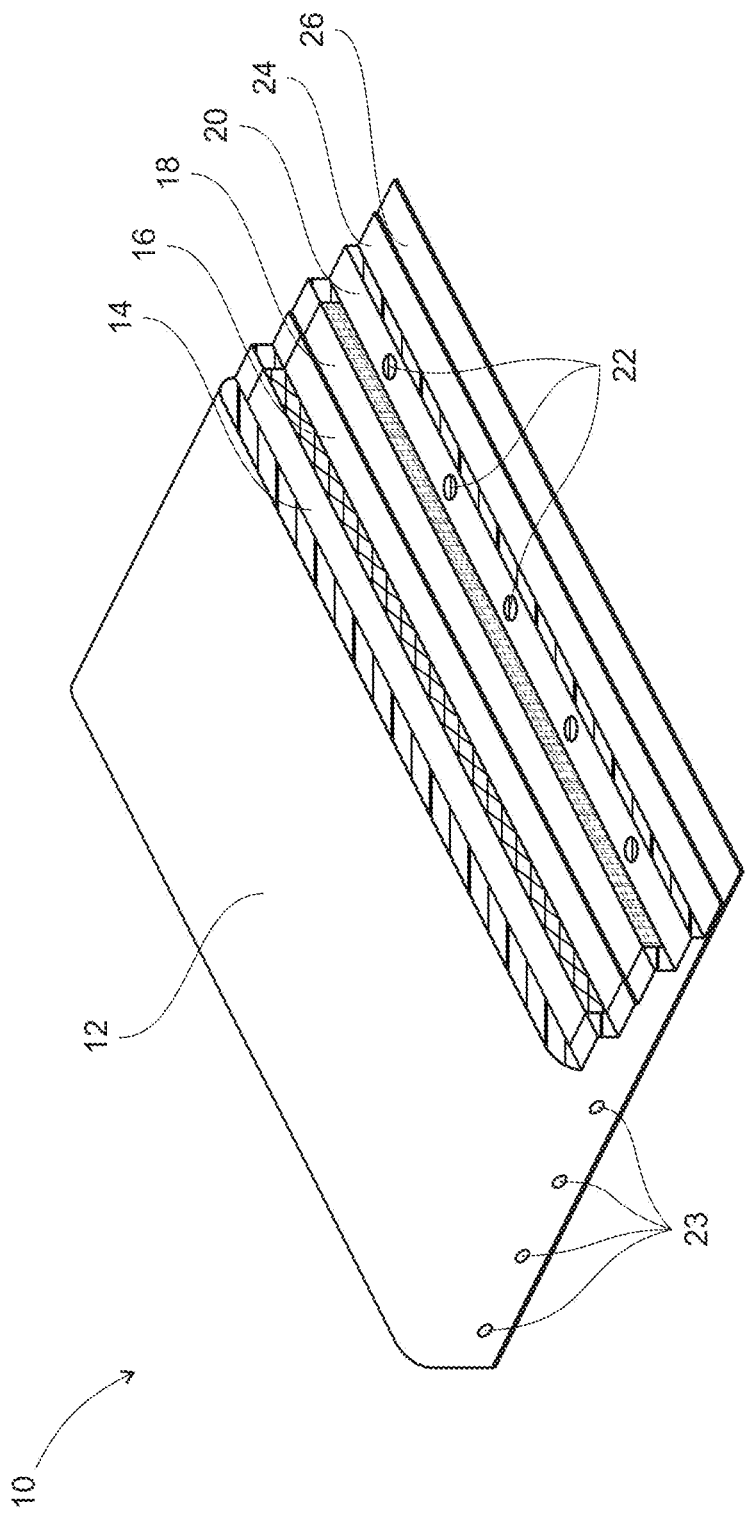
FIG. 1 is a perspective view of an embodiment of a wound closure device illustrating the magnet layer, insulation layer, absorbent layer, polymer layer, adhesive layer, and removable cover.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another elements as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

A wound closure device is provided for closing wounds without sutures. FIG. 1 and FIG. 2 depict one embodiment of a wound closure device 10 in perspective view and cross-sectional view, respectively. The wound closure device 10, (illustrated as a first and second elongated strip 11, 40 in FIG. 4 and FIG. 5) has a polymer enclosure 12. The enclosure 12 may be made of any one of number of polymers, but in a preferred embodiment is a silicone enclosure 12. Other materials for an enclosure may be made from natural or synthetic polymers including rubber, neoprene, polyvinyl chloride, polyvinyl butyral, polystyrene, polyethylene, polypropylene, nylon, polyacrylonitrile. Within the enclosure 12 is a magnet 14, which may be a single magnet or a segmented magnet (as illustrated in FIG. 3 as 14a and 14b). The magnet 14 may be made from a number of materials, such as ferromagnetic materials, or rare-earth elements, such as magnets made from alloys of neodymium, iron and boron. The advantage of rare-earth magnets, such as neodymium magnets is that their crystalline structures have very high magnetic anisotropy and can retain high magnetic moments in the solid state.

In a preferred embodiment, the magnet is a flexible magnet that is rolled or extruded in a magnetic film, and then cut to size into a magnetic sheet or strip. In one composition of a magnet useful for wound closure comprises NdFeB magnetic powder, chlorinated polyethylene (CPE), and an annexing agent such as soybean oil.

In a preferred embodiment the magnet in the device is comprised of approximately 90.5% NdFeB powder, 8.5% CPE, and 1% annexing agent. In one embodiment, the NdFeB powder may be comprised of approximately 31.0-31.8% PrNd, approximately 64-66.5% Fe, approximately 1.00-1.03% B, approximately 1.5-1.8% Dy, approximately 0.5-0.8% Co, approximately 0-0.25% Nb, and approximately 0.0-0.2% Al. Deviations from the percentages above that also allow for a strong but flexible magnet are allowed and known by persons having ordinary skill in the art.

Adjacent and above the magnet 14 is an insulation layer 16. The insulation layer is a vapor barrier protective layer that is waterproof and prevents moist secretions from getting absorbed by the magnet 14. If moisture contacts the magnet 14, the magnet may rust, and the magnetic material may leak into the absorbent layer 18. The insulating layer 16 may be made from any number of waterproof materials known in the art, such as nylon or other waterproof polymers.

Adjacent to the insulation layer 16 is an absorbent layer 18, which can absorb wound secretions. The absorbent layer 16 may be made from a variety of absorbent materials, including sterile gauze sponge, cotton, cellulose fibers, wool, silk, linen, acetate, nylon, and polyester materials. Adjacent and under the absorbent layer 18 is a polymer layer 20, which has a plurality of holes 22 that allow for draining of potential build-up of secretions from a wound. The plurality of holes (or pores) 22 create a passageway from the absorbent layer 18 through the polymer layer 20, through the adhesive layer 24, to the skin of the patient. Capillary action allows the absorbent layer 18 to absorb potential secretions from the wound via the capillary properties of the absorbent layer 18, and then diffuse the secretions via plurality of holes 22 in the device. There may also be a plurality of side holes 23 on the side surfaces of the polymer enclosure 12 that allow fluids not to only drain potential buildup to and from the surface of the skin, but drain fluids out of the sides of the device 10 as illustrated in FIG. 1 and FIG. 2.

The polymer layer 20 on the bottom of the device 10 may be contiguous with the polymer enclosure 12 that houses the magnet 14, insulation layer 16, and absorbent layer 18. On the bottom surface of the polymer layer 20 is an adhesive surface layer 24. The adhesive surface 24 allows the magnetic wound closure device 10 to adhere to the skin of a patient, adjacent to a wound. The adhesive layer 24 may be made from any one of a number of adhesive compositions, including: reusable adhesives, pressure sensitive adhesives, contact adhesives, resins, epoxies, polyurethane, cyanoacrylate (CA), polymers, acrylic-based adhesives that cure under ultraviolet (UV) light, silicone based adhesives, and polyolefinic polymers. Protecting the adhesive layer 24, is a removable cover 26, such as peel-off tape, that protects the adhesive layer 24 from the environment, and prevents the adhesive from sticking to any surface until the cover 26 is removed. The practitioner removes this adhesive cover 26 before placing the device 10 on the patient's skin.

FIG. 3 illustrates one embodiment of the magnet 14 showing segmented magnet portions 14a, 14b, in cross sectional view. Each individual magnetic segment 14a, 14b is adjacent to a different segment within the polymer enclosure 12 (the non-magnetic elements within the polymer enclosure, illustrated in FIGS. 1 and 2, are not shown in FIG. 3, but may exist on one or more embodiments previously described and illustrated). The polymer enclosure 12 is comprised of a flexible polymer that allows for the polymer to flex when the magnet 14 within the polymer bends. The inclusion of plasticizers within the polymer composition of the enclosure 12 lowers the glass transition temperature ($T_g$) of the polymer, therefore allowing device 10 to flex when the magnet 14 within the polymer enclosure 12 flexes. Plasticizers are commonly known and used in the art, and may included phthalate ester plasticizers commonly used in medical devices such as: dicarboxylic/triboxylic ester-based plasticizers, including Bis (2-ethylhexyl) phthalate, Di-n- butyl phthalate, or Diisooctyl phthalate. The segmented magnet 14a, 14b has a spacer region 50 (which may be a void to allow movement) between the each magnet segment 14a, 14b, which allows the segments 14a, 14b of the magnet 14 to flex horizontally and vertically. This flexing is useful for easy placement of the device 10 on a patient's skin. One advantage of a segmented magnet 14a, 14b, having greater flexibility compared to a non-segmented magnet 14 is that the segmentation allows the practitioner to align the device 10 along a non-linear wound (i.e., a wound that traverses a curved surface on a patient, such as the curved features of an arm, or a leg), since the segments 14a, 14b combined with the voids 50 between each segment 14a, 14b, can curve to match the shape of non-linear wound. Shaping the device 10 to match the wound is advantageous because a pair of devices 10 can be placed in closer proximity to each other across a wound that is irregularly shaped if each device 10 is capable of flexing to match the shape of the wound.

Figure 4:
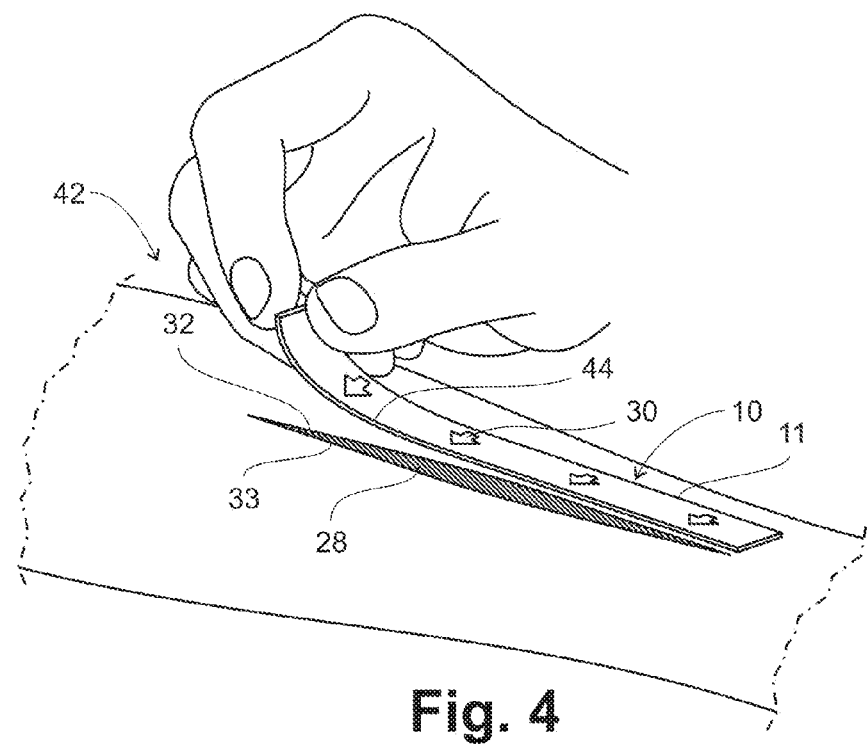
FIG. 4 is a perspective exemplary view of one magnetic wound closure device being placed one side of a patient's wound.
Figure 5:
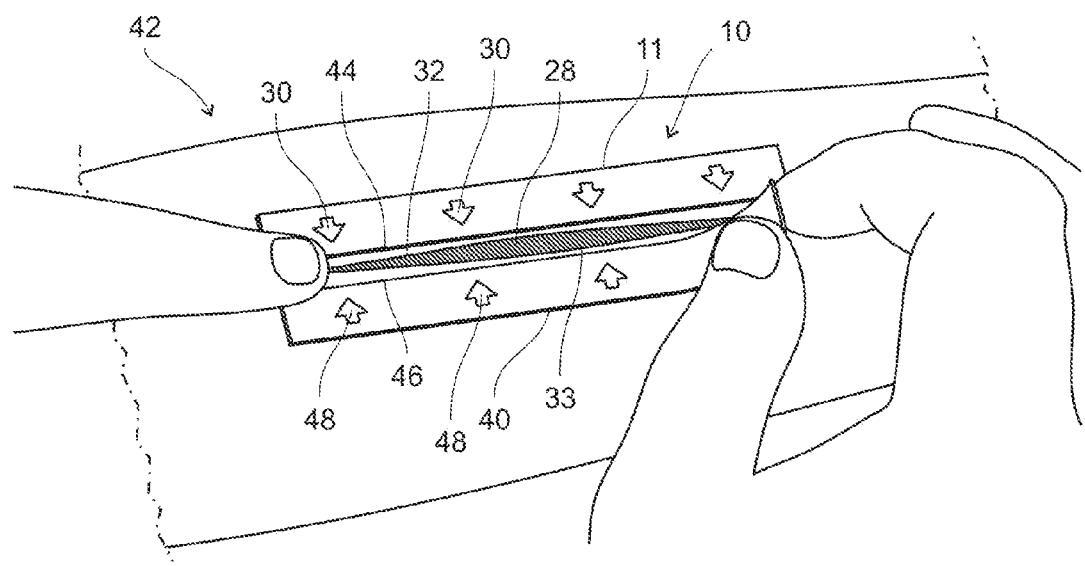
FIG. 5 is a perspective exemplary view of two magnetic wound closure devices, each one placed on an opposite side of a wound, and oriented in opposite polarity to each other such that the two magnetic wound closure devices attract each other, thereby reapproximating wound edges.

FIG. 4 illustrates the placement of a first strip 11 of the magnetic wound closure device 10 on an arm 42 of a patient, adjacent to a wound 28. The strip 11 has a directional indicator 30, here illustrated as plurality of arrows pointing toward a first edge 32 of the wound 28. The inner edge 44 of the first strip 11 is placed across from the inner edge 46 of a second strip 40, which also has directional indictors 48 pointing toward a second edge 33 of the wound 28. When using two strips 11, 40, the directional indicators 30 of the first strip 11, and the directional indicators 48 of a second strip 48 are oriented such that they point toward each other, thereby ensuring that the inner edges 44, 46 of each strip 11, 40 are magnetically polar opposites of each, and thus attract each other, thereby drawing in the edges 32, 33 of the wound 28 together. If the strips 11, 40 are not oriented correctly (i.e. the north pole edge of the first strip 11 across from the the north pole of the second strip 40), then when the strips 11, 40 are placed on opposite sides of a wound, the strips 11, 40 would repel each other instead of attract each other, thus hindering wound recover.

Since the strips 11, 40 are secured to the patient's skin via an adhesive layer 24, when the strips 11, 40 attract each other, the edges of the wound 28 are drawn together as the strips 11, 40 are magnetically drawn together. The strips 11, 40 can easily be applied by a practitioner, peeled off the patient if required, and reapplied if necessary. Since no sutures or staples are used when applying the strips 11, 40, the strips 11, 40 are advantageous for emergency situations when medical personnel are overloaded, or even in non-emergency situations for use with young children who would be more apprehensive regarding traditional wound closure devices and methods. The strips 11, 40 also do not require costly biohazard disposal, and cause less trauma. The strips 11, 40 can be used not only on human patients, but animals as well.

The dimensions of the strips 11, 40 can be of any length, but preferable between 3 cm and 10 cm in length, and 1 cm and 3 cm in width. Preferably, the height of the each magnetic wound closure strip 11, 40 is between 0.5 mm and 5 mm, and preferably approximately 1 mm in height. A thin strip 11, 40, allows each strip 11, 40 to be flexible, and to lay substantially flat on the patient's skin. This is advantageous because flat strips 11, 40 prevent catching or snagging on clothing or other objects. In another preferred embodiment, the dimensions of the magnetic wound closure strips 10, 40 are approximately 4 cm in length, 2 cm in width, and 1 mm in height.

Each component of the strips 11, 40 can have dimensions that accommodate the size of the patient and size of the wound. In one embodiment, the magnet 14 within each strip 11, 40 has a height of approximately 0.04 cm, a length of approximately 1.6 cm and width of approximately 0.8 cm. In one embodiment, the absorbent layer 18 is approximately 0.04 cm thick, the adhesive layer 16 is approximately 0.001 cm thick, the insulation layer 18 is approximately 0.001 cm thick, and the peelable cover 26 is approximately 0.003 cm thick.

While the invention has been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

I claim:

1. A magnetic wound closure device comprising:
   i) a magnet;
   ii) an insulation layer adjacent to said magnet;
   iii) an absorbent layer adjacent to said insulation layer;
   iv) a polymer layer adjacent to said insulation layer, said polymer layer having a plurality of holes capable of draining wound secretions to or from said absorbent layer; and,
   v) an adhesive layer adjacent to a bottom surface of said polymer layer, said adhesive layer capable of adhering to a patient's skin,
   vi) a polymer enclosure containing at least said magnet, said insulation layer, and said absorbent layer;
   wherein the magnet is an elongated flexible magnetic strip capable of flexing both vertically and horizontally, and wherein the elongated flexible magnetic strip is capable of flexing around a curve of a wound edge;
   whereby a first and second magnetic wound closure device oriented in opposite polarity to each other, and adhered to skin on opposite sides of a wound, functions to reapproximate wound edges when the first and second magnet wound closure devices attract each other, thereby drawing edges of the wound together to improve wound healing.

2. The magnetic wound closure device of claim 1, wherein said magnet is characterized as having a plurality of magnetic segments capable of flexing within said polymer enclosure, whereby said device may be aligned along a non-linear wound.

3. The wound closure device of claim 1, further comprising a removable adhesive cover adjacent to said adhesive layer.

4. The wound closure device of claim 1, wherein said polymer layer is a silicone layer.

5. The wound closure device of claim 1, wherein said polymer enclosure is made of a silicone.

6. The wound closure device of claim 1, wherein said wound closure device further comprises a directional indicator for determining a correct magnetic alignment of said wound closure device with respect a second wound closure device.

7. The magnetic wound closure device of claim 1, wherein the magnet is characterized as a neodymium magnet.

8. The magnetic wound closure device of claim 1, wherein the elongated flexible magnetic strip has dimensions in the range of between 3 cm and 10 cm in length and 1 cm and 3 cm in width.

9. The magnetic wound closure device of claim 7, wherein the neodymium magnet is characterized as being formed from NdFeB magnetic powder, chlorinated polyethylene (CPE), and an annexing agent.

10. The magnetic wound closure device of claim 9, wherein the neodymium magnet is characterized as comprising approximately 90.5% NdFeB powder by weight, approximately 8.5% CPE by weight, and approximately 1% annexing agent by weight.

11. A magnetic wound closure device comprising:
i) a neodymium magnet;
ii) an insulation layer adjacent to said magnet;
iii) an absorbent layer adjacent to said insulation layer;
iv) a polymer layer adjacent to said insulation layer, said polymer layer having a plurality of holes capable of draining wound secretions to or from said absorbent layer; and,
v) an adhesive layer adjacent to a bottom surface of said polymer layer, said adhesive layer capable of adhering to a patient's skin,
vi) a polymer enclosure containing at least said magnet, said insulation layer, and said absorbent layer,
vii) a removable adhesive cover adjacent to said adhesive layer;
viii) a directional indicator for determining a correct magnetic alignment of said wound closure device with respect to a second wound closure device;
ix wherein the magnet is an elongated flexible magnetic strip capable of flexing both vertically and horizontally, and wherein the elongated flexible magnetic strip is capable of flexing around a curve of a wound edge;
wherein the elongated flexible magnetic strip has dimensions in the range of between 3 cm and 10 cm in length and 1 cm and 3 cm in width;
wherein said magnet is characterized as having a plurality of magnetic segments capable of flexing said magnetic wound closure device.

\* \* \* \* \*